(12) United States Patent
Smith et al.

(10) Patent No.: US 6,491,874 B1
(45) Date of Patent: Dec. 10, 2002

(54) MULTI-LIMBED REACTION VESSEL

(75) Inventors: Gillian Elizabeth Smith, Bishop's Stortford (GB); Kenneth Thomas Veal, Fyfield (GB)

(73) Assignee: SmithKline Beecham p.l.c. (GB)

( * ) Notice: Subject to any disclaimer, the term of this patent is extended or adjusted under 35 U.S.C. 154(b) by 0 days.

(21) Appl. No.: 09/508,181

(22) PCT Filed: Sep. 11, 1998

(86) PCT No.: PCT/EP98/05861

§ 371 (c)(1),
(2), (4) Date: Mar. 7, 2000

(87) PCT Pub. No.: WO99/15274

PCT Pub. Date: Apr. 1, 1999

(30) Foreign Application Priority Data

Sep. 19, 1997 (GB) .............................................. 9719981

(51) Int. Cl.$^7$ .................................................. B01L 3/00
(52) U.S. Cl. ........................ 422/102; 422/104; 422/129; 422/189
(58) Field of Search .......................... 422/61, 102, 104, 422/129, 189

(56) References Cited

U.S. PATENT DOCUMENTS

| | | |
|---|---|---|
| 3,034,868 A | 5/1962 | Erickson |
| 4,230,664 A * | 10/1980 | Cais .............................. 422/61 |
| 4,687,986 A | 8/1987 | Ericksson |
| 4,871,516 A | 10/1989 | Murib |

FOREIGN PATENT DOCUMENTS

| | | |
|---|---|---|
| DE | 905 547 | 3/1954 |
| EP | 0 391 331 | 10/1990 |
| GB | 803370 | * 10/1958 |
| WO | WO 97/04863 | 2/1997 |

* cited by examiner

*Primary Examiner*—David A. Reifsnyder
(74) *Attorney, Agent, or Firm*—James M. Kanagy; Charles M. Kinzig

(57) ABSTRACT

A laboratory vessel comprising two substantially cylindrical chambers with parallel longitudinal axes between their bottom and mouth openings and lower and upper conduits linking the chambers so that he contents of the vessel can flow between the first and second chambers via the upper and lower conduits. The vessel is particularly suited for use with automated reactor systems.

16 Claims, 2 Drawing Sheets

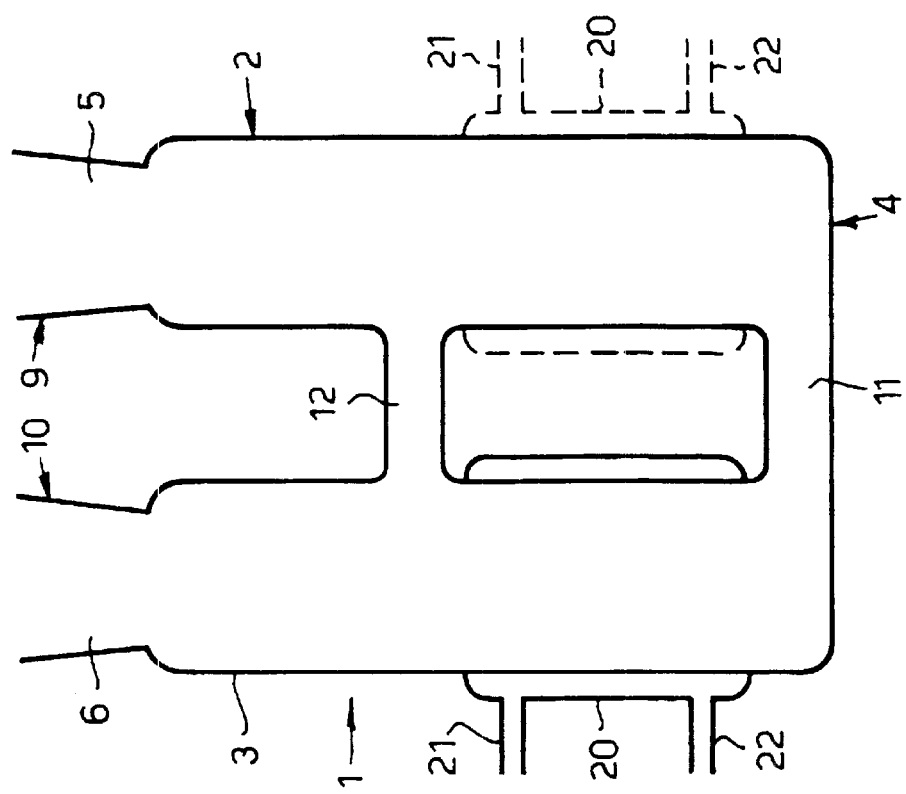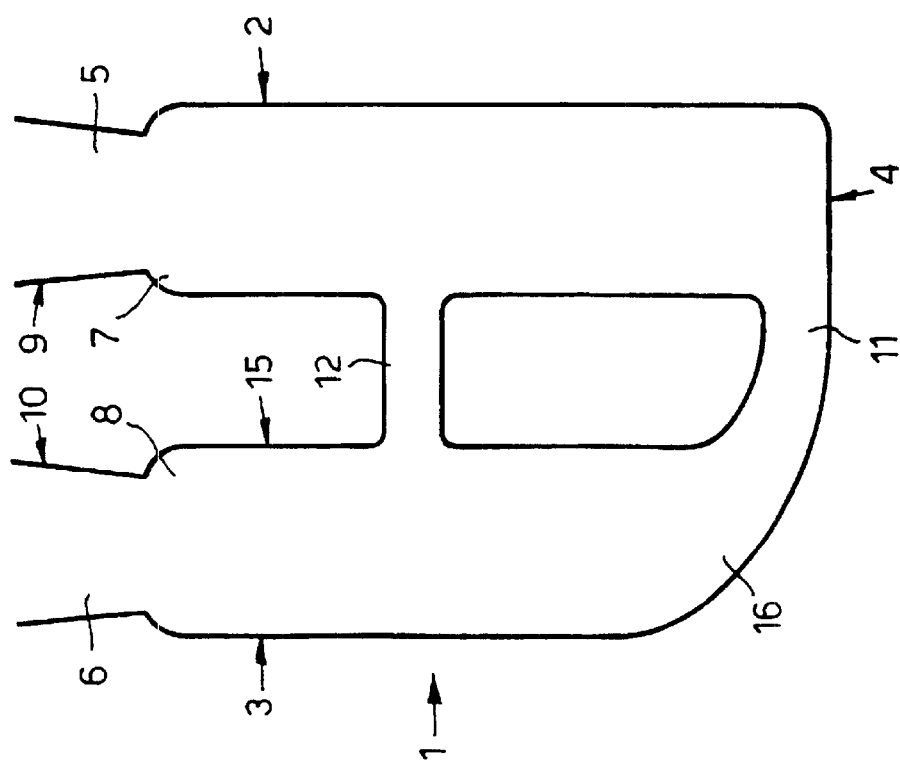

MULTI-LIMBED REACTION VESSEL

Figure 2:
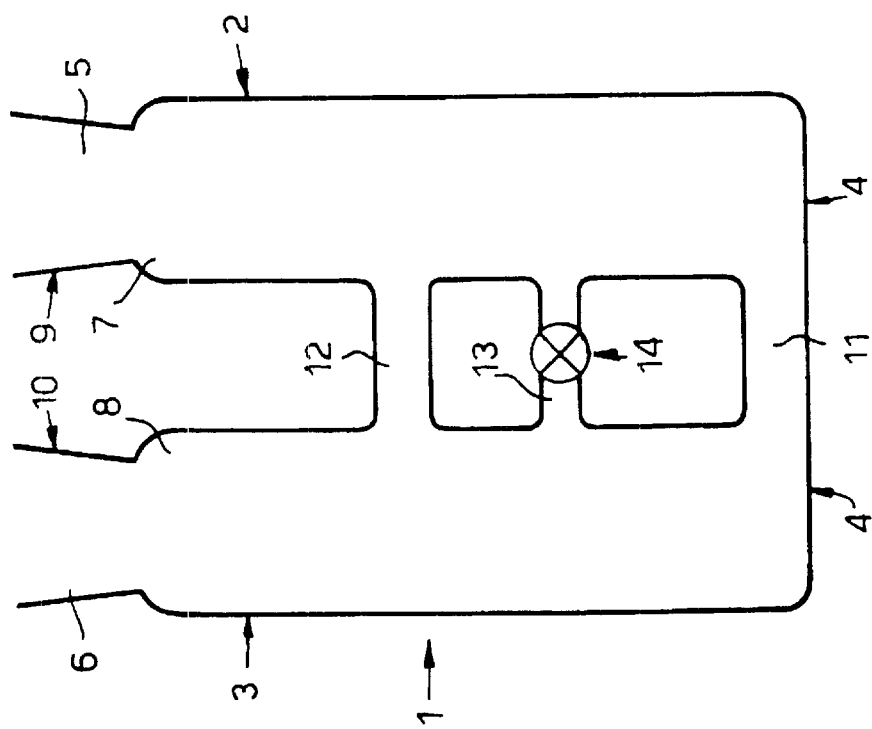

This invention relates to a novel device, being a laboratory reaction vessel suitable for use in chemical reactions at a laboratory scale.

Laboratory glassware of various constructions and functions is known. Multilimbed vessels such as "U" tubes have long been known, as have vessels with side arms and other means to achieve circulation through the vessel to promote thorough mixing, sampling etc. Examples of such apparatus are disclosed in GB 803370, U.S. Pat. Nos. 4,230,664 and 4,871,516. Most of such glassware has been designed for classical benchtop chemistry, but the advent of laboratory automation has meant that such classical glassware is not optimum for modern laboratories.

It is an object of this invention to provide a novel laboratory reaction vessel which is more suitable for use in an automated laboratory.

According to this invention a laboratory vessel comprises a first chamber and a second chamber, each said chamber having a mouth opening adjacent an upper part of the chamber opposite the bottom of the chamber, the first and second chambers being connected by an integral lower conduit which links adjacent lower parts respectively of the first and second chambers, and by an integral upper conduit which links adjacent upper parts respectively of the first and second chambers such that fluid contents of the vessel can flow between the first and second chambers via the upper and lower conduits.

The first and second chambers may be of the same or different volumes, shapes, widths or lengths (length being defined along the axis of the mouth opening and the bottom of the chamber, and width perpendicular to the length). For example one chamber may be larger than the other and may be used for the insertion of a stirrer through its mouth opening, allowing the other chamber to be accessed by a laboratory automation robot or other device. For example the relative volumes of the chambers may be in the approximate ratio 1.5:1. The first and second chambers are preferably longitudinally elongated chambers, for example tubular chambers, e.g. preferably cylindrical chambers. Such tubular chambers may for example have a rounded or flat bottom.

The construction of the mouth opening of respectively the first and second chambers may be the same or different. For example the mouth opening of each may comprise a standard laboratory female or male connector, e.g. a "Quickfit™" type connector, a flange connector, a gland or screw threaded connector etc. Suitably the mouth opening is at the upper end of its chamber, and faces in the direction of the longitudinal axis of the chamber, for example in the case of cylindrical chambers, suitably being coaxial with the chamber. Each chamber may have more than one mouth opening. In the vessel of the invention preferably the first and second chambers have their respective longitudinal axes aligned substantially parallel to each other, e.g. the longitudinal axes of cylindrical chambers may be so aligned.

The lower and upper conduits may comprise tubular conduits connecting the chambers. Such tubular conduits may have their longitudinal axes aligned substantially parallel. When the first and second chambers have their longitudinal axes aligned substantially parallel, the axes of the upper and lower conduits, preferably the axes of both conduits may be aligned substantially perpendicular to the longitudinal axes of the chambers. The lower conduit may be adjacent to the bottom of one or both of the first or second chambers. The upper conduit may link upper parts of the chambers adjacent to the respective mouth openings, or any part between the mouth opening and the lower conduit, e.g. parts ca. half way up the chamber. The bore of the conduits is suitably less than the width of the first and/or second chambers.

For example in one construction of the vessel of the invention the vessel may take the form of a "U" tube, with an upper conduit linking the limbs of the U in a direction perpendicular to the limbs of the U, with the lower bend of the U comprising the lower conduit.

Therefore one preferred form of the vessel of the invention comprises two chambers being:

a first substantially cylindrical chamber having a first longitudinal axis defined between the bottom and an upper mouth opening thereof, a second substantially cylindrical chamber having a second longitudinal axis defined between the bottom and an upper mouth opening thereof, the first and second longitudinal axes being substantially parallel;

a lower integral conduit linking respective lower parts of the first and second chambers, and an upper integral conduit linking respective upper parts of the first and second chambers above the lower conduit, such that fluid contents of the vessel can flow between the first and second chambers via the upper and lower conduits.

For example in another construction of the vessel of the invention the first chamber may be substantially cylindrical, and the second chamber may have a substantially cylindrical upper part above the upper conduit, and a lower part below the upper conduit which curves toward and joins the first chamber, such that for example the second chamber is of an overall generally "J" shape, with the lower curved part of the "J" connecting with the first chamber and comprising the lower conduit. This curved shape can assist with circulation of liquid content in the vessel and avoid the deposition of solid deposits etc. in the second limb.

In another embodiment the vessel may have a median conduit located between the upper and lower conduits, and connecting parts of the first and second chambers which are part way between the upper and lower conduits, either midway between or closer to either the upper or lower conduit, relative to the length of the chambers. The median conduit may be similar in construction and/or dimensions to the upper and lower conduits.

The upper and/or lower and/or median conduit (if present) may incorporate valve means such as taps to control, direct, restrict or close off flow through the conduit.

The purpose of such a median conduit is inter alia principally to enable the contents of the vessel to be circulated between the chambers when it contains insufficient liquid content to reach the level of the upper conduit and so may be difficult to cause to flow through the upper conduit. For example a first volume of liquid may be introduced into the vessel, insufficient to reach the upper conduit but sufficient to reach the lower and the median conduit. The liquid content may then be circulated through the lower and median conduits. A second volume of liquid may then be introduced, sufficient to reach the upper conduit, and the median conduit may then be closed off, e.g. by a valve means in the median conduit to allow circulation to take place via the upper and lower conduits.

One or both of the chambers may include other features used in chemical reactors, e.g. multiple mouth openings, a thermocouple, a thermometer pocket, side arms for introduction of gases, optical windows e.g. flat surfaces, etc. The conduits, for example the upper and/or median conduit (if present) may also incorporate such features, e.g. a thermocouple. One or both of the chambers may for example incorporate fittings in their walls, e.g. in their respective bottoms, e.g. screw connections to allow instruments such as optical or other instruments to be fitted in direct contact with the liquid content in the chamber.

In a further variant, the vessel of the invention may be provided with one ore more external heating or cooling jackets, for example located around the first and/or second chamber, and/or around a conduit. Such a cooling/heating jacket may comprise a sleeve, e.g. of glass if the chamber or conduit is made of glass, around the chamber or conduit, provided with an inlet and outlet by which a heating or cooling fluid e.g. hot or cold water may respectively enter and exit. The jacket may be fused to the wall of the chamber or conduit.

In a further embodiment one or more of the conduits, suitably the lower conduit, may incorporate an internal stirrer or impeller to cause the fluid content to circulate, e.g. in the form of an impeller freely rotatable in the conduit e.g. by means of an external rotatable magnet magnetically coupled to a magnetic drive element on the impeller. When such an impeller is rotated by the external magnet it can cause circulation of liquid content without the need to insert a stirrer through a mouth opening of the vessel.

The vessel of the invention is particularly suited to circulating a fluid content, e.g. from the first chamber through the lower conduit into the second chamber and then back into the first chamber through the upper or median conduit and so on in a circulatory manner. For this purpose one or both of the mouth openings may be made of suitable dimensions and construction for the insertion of an impeller-type stirrer into fluid content in the first or second chamber. The vessel of the invention also facilitates the addition/removal of liquid content via one mouth opening whilst the other is for example fitted with a stirrer or reflux condenser etc.

The invention also provides a method of use of a vessel as described above for the performance of a chemical reaction between substances contained therein.

The vessel of the invention is found to be particularly suited for use with an automated laboratory system including robot means to introduce or extract substances into the vessel or to perform other operations and/or tests on liquid content in the vessel, and a holder, said robot means and holder being moveable relative to each other, to move the vessel into a cooperation position with one or more such robot means.

The vessel of the present invention may conveniently be integrally made of glass by conventional glassblowing techniques. Alternatively the vessel may be made of other suitable materials such as stainless steel or other inert metals, or of inert plastics materials such as PTFE.

Figure 1:
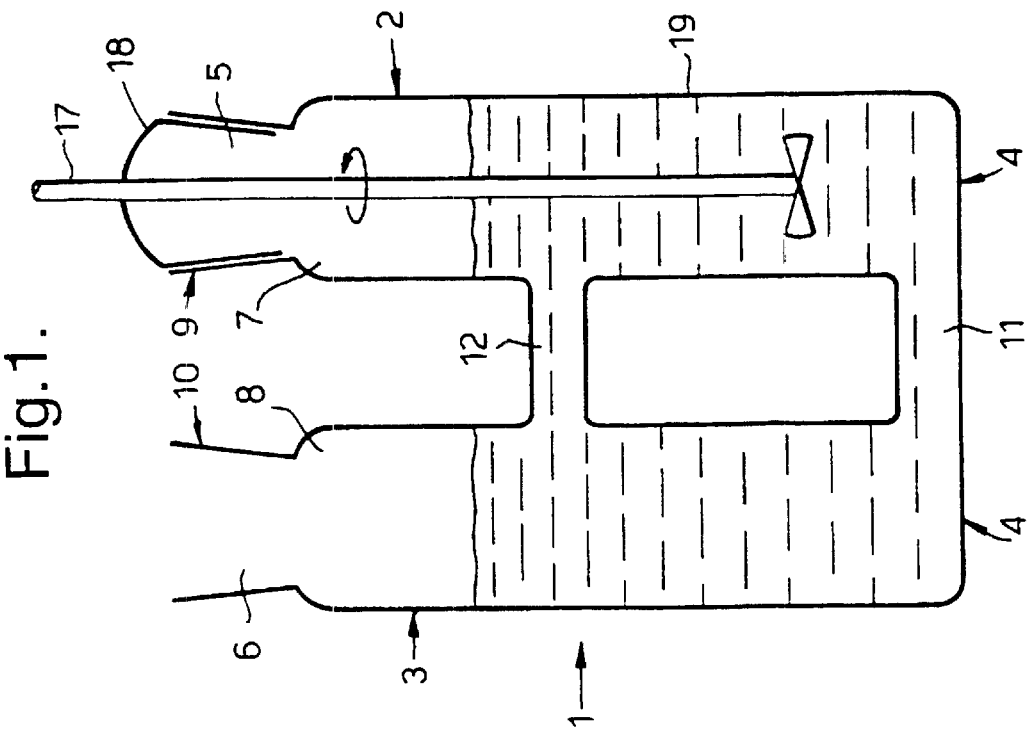

The invention will now be described by way of example only with reference to the accompanying drawings which show:

FIG. 1 a longitudinal section of a vessel of the invention.

FIG. 2 a longitudinal section of a vessel of the invention having a median conduit.

FIG. 3 a longitudinal section of another vessel of the invention.

FIG. 4 a longitudinal section of a vessel of the invention having an integral cooling/heating jacket.

Referring to FIGS. 1, 2 and 3, a laboratory vessel, 1 overall, of this invention is shown. The vessel 1 comprises a first chamber 2 and a second chamber 3, being cylindrical chambers with a flat bottom 4, their respective longitudinal axes being aligned parallel to each other. Each chamber 2, 3 has a mouth opening 5, 6 adjacent an upper part 7, 8 of the chamber 2, 3 opposite the bottom 4 of the chamber 2, 3, the chambers being elongated along the mouth-bottom axis. The first and second chambers 2, 3 as shown are approximately the same volume, (ca. 100 ml each) and the same cylindrical shape.

The mouth opening 5, 6 of each chamber is at the upper end of its chamber 2, 3, and faces in the direction of the longitudinal axis of the chamber, being coaxial with the chamber 2, 3. The mouth opening of both the first and second chambers 2, 3 as shown are standard laboratory female ground glass connector 9, 10. The mouth openings 5, 6 may alternatively each independently comprise for example flange connectors, septum connectors etc. (not shown).

The first and second chambers 2, 3 are connected by an integral lower conduit 11 which links adjacent lower parts respectively of the first and second chambers 2, 3, and by an integral upper conduit 12 which links adjacent upper parts respectively of the first and second chambers 2, 3. Fluid contents of the vessel 1 can consequently flow between the first and second chambers 2, 3 via the upper and lower conduits 11, 12. The conduits 11, 12 comprise cylindrical tubular conduits connecting the chambers, with their longitudinal axes aligned parallel and perpendicular to the longitudinal axes of the chambers. The lower conduit 11 is adjacent to the bottom of both of the first or second chambers. The upper conduit 12 links upper parts of the chambers 2, 3 between the mouth opening and the lower conduit. The bore of the conduits 11, 12 is less, e.g. being ca. 1 cm, than the width of the first and/or second chambers 2, 3.

In FIG. 2 a vessel 1 is shown having a median conduit 13, similar in construction to the upper and lower conduits 11, 12, but connecting parts of the first and second chambers 2, 3 which are part way between the upper and lower conduits 11, 12. The median conduit 13 is shown incorporating a tap 14 to control, restrict or close off flow through the conduit 13, the tap 14 being optional.

In FIG. 3 a vessel 1 is shown in which the first chamber 2 is substantially cylindrical with a flat bottom 4, and the second chamber 3 has a substantially cylindrical upper part 15 above the upper conduit 12, and a lower part 16 below the upper conduit 12 which curves toward and joins the first chamber 2, such that the second chamber 3 is of an overall generally "J" shape, with the lower curved part 16 of the J connecting with the bottom 4 of the first chamber 2 and comprising the lower conduit 11.

In FIG. 1 the vessel 1 is shown in use. The mouth opening 5 is of suitable dimensions and construction for the insertion of an impeller-type stirrer 17, having a male ground glass connector gland (shown schematically 18) fitting corresponding to the connector 9, into fluid content 19 in the first chamber 2. For example the connector 9 may be a B24 ground glass cone. Activation of the stirrer 17 causes circulation of fluid content 19 from the first chamber 2 through the lower conduit 11 into the second chamber 3 and then back into the first chamber 2 through the upper conduit 12 and so on in a circulatory manner in the direction of the arrows, for example in the direction of the arrow (or in the reverse direction).

The mouth opening 6 may for example be a B14 ground glass cone, and may be fitted with a reflux condenser or other apparatus (not shown). In an alternative mode of use the shaft of such a stirrer may be surrounded by a condenser, thereby leaving the other mouth opening free for access by for example a sampling device or other fitting. The upper conduit 12 may have a thermocouple (not shown) built into its walls.

Referring to FIG. 4 a vessel of the invention as shown in FIG. 1 (corresponding features being numbered correspondingly) is shown, having an external cooling/heating jacket 20 around the first chamber 2. The cooling/heating jacket 20 comprises a sleeve, e.g. of glass if the chamber 2 is made of glass, around the chamber 2 provided with an inlet 21 and outlet 22 by which a heating or cooling fluid e.g. hot or cold water may respectively enter and exit. The jacket 20 may be fused to the wall of the chamber 2. The second chamber 3 may also be provided with such a heating/cooling jacket 20 as shown in dotted lines. One or both of the jackets 20 may be continued up above the level of the upper conduit 12. A similar cooling/heating jacket may also be provided around the conduit 12.

What is claimed is:

1. A laboratory vessel comprising a first chamber and a second chamber, each chamber having a bottom and, a mouth opening adjacent an upper part of the chamber opposite the bottom of the chamber, each chamber having a longitudinal axis between the bottom and the mouth opening, the first and second chambers being connected by an integral lower conduit which links adjacent lower parts respectively of the first and second chambers, and by an integral upper conduit which links adjacent upper parts respectively of the first and second chambers such that fluid contents of the vessel can flow between the first and second chambers via the upper and lower conduits, and the vessel has a median conduit connecting parts of the first and second chambers which are part way between the upper and lower conduits.

2. A vessel according to claim 1 characterised in that the chambers are cylindrical chambers.

3. A vessel according to claim 1 characterised in that the mouth opening is at the upper end of its chamber, and faces in the direction of the longitudinal axis of the chamber.

4. A vessel according to claim 1, characterised in that the first and second chambers have their respective longitudinal axes aligned parallel to each other.

5. A vessel according to claim 1 characterised in that the lower and upper conduits comprise tubular conduits connecting the chambers and extending in a conduit length direction between the chambers.

6. A vessel according to claim 5 characterised in that the tubular conduits have their conduit length directions aligned parallel.

7. A vessel according to claim 6 characterised in that the axes of the upper and lower conduits, are aligned perpendicular to the longitudinal axes of the chambers.

8. A vessel according to claim 1 characterised by a first chamber and a second chamber being: a first substantially cylindrical chamber having a bottom and an upper mouth opening and having a first longitudinal axis defined between the bottom and the upper mouth opening thereof; a second substantially cylindrical chamber having a bottom and an upper mouth opening and having a second longitudinal axis defined between the bottom and the upper mouth opening thereof, the first and second longitudinal axes being substantially parallel; the first and second chambers being connected by a lower integral conduit linking respective lower parts of the first and second chambers, and the first and second chambers being connected by an upper integral conduit linking respective upper parts of the first and second chambers above the lower conduit, such that fluid contents of the vessel can flow between the first and second chambers via the upper and lower conduits, and the first and second chambers being connected by a median conduit connecting parts of the first and second chambers which are part way between the upper and lower conduits.

9. A vessel according to claim 1 characterised in that the lower conduit is adjacent to the bottom of one or both of the first or second chambers.

10. A vessel according to claim 1 characterised in that the vessel takes the form of a "U" tube, with an upper conduit linking the limbs of the U in a direction perpendicular to the limbs of the U, with the lower bend of the U comprising the lower conduit.

11. A vessel according to claim 1 characterised in that the first chamber is substantially cylindrical, and the second chamber has a substantially cylindrical upper part above the upper conduit, and a lower part below the upper conduit which curves toward and joins the first chamber.

12. A vessel according to claim 1 characterised in that the vessel has a median conduit connecting parts of the first and second chambers which are part way between the upper and lower conduits.

13. A vessel according to claim 1 characterised in that the upper and/or lower conduit, with or without a median conduit, incorporates valve means to control, restrict or close off flow through the conduit.

14. A vessel according to any one of the preceding claims, characterised in that there is an external cooling/heating jacket around one or both of the first or second chambers or around a conduit thereof.

15. Use of a vessel according to claim 1 for circulating a fluid content from the first chamber through the lower conduit into the second chamber and then back into the first chamber through the upper or median conduit and so on in a circulatory manner.

16. A method of use of a vessel according to claim 1 for performing a chemical reaction between substances contained therein.

* * * * *